United States Patent
DeBusschere et al.

(10) Patent No.: US 9,848,780 B1
(45) Date of Patent: Dec. 26, 2017

(54) ASSESSING CARDIOVASCULAR FUNCTION USING AN OPTICAL SENSOR

(71) Applicant: Google, Inc., Mountain View, CA (US)

(72) Inventors: Brian Derek DeBusschere, Los Gatos, CA (US); Jeffrey L. Rogers, San Carlos, CA (US)

(73) Assignee: Google Inc., Mountain View, CA (US)

( * ) Notice: Subject to any disclaimer, the term of this patent is extended or adjusted under 35 U.S.C. 154(b) by 0 days.

(21) Appl. No.: 14/681,625

(22) Filed: Apr. 8, 2015

(51) Int. Cl.
*A61B 5/0205* (2006.01)
*A61B 5/024* (2006.01)
*A61B 5/00* (2006.01)
*A61B 5/103* (2006.01)
*A61B 5/11* (2006.01)
*A61B 5/021* (2006.01)

(52) U.S. Cl.
CPC .......... *A61B 5/0205* (2013.01); *A61B 5/0077* (2013.01); *A61B 5/021* (2013.01); *A61B 5/02427* (2013.01); *A61B 5/02433* (2013.01); *A61B 5/1032* (2013.01); *A61B 5/1102* (2013.01)

(58) Field of Classification Search
CPC ....... A61B 5/0205; A61B 5/077; A61B 5/021; A61B 5/02433; A61B 5/1032; A61B 5/11
USPC ......................................................... 600/301
See application file for complete search history.

(56) References Cited

U.S. PATENT DOCUMENTS

| | | |
|---|---|---|
| 5,121,124 A | 6/1992 | Spivey et al. |
| 5,410,471 A | 4/1995 | Alyfuku et al. |
| 5,798,798 A | 8/1998 | Rector et al. |
| 6,254,544 B1 | 7/2001 | Hayashi |
| 6,313,825 B1 | 11/2001 | Gilbert |
| 6,386,757 B1 | 5/2002 | Konno |
| 6,513,970 B1 | 2/2003 | Tabata et al. |
| 6,524,239 B1 | 2/2003 | Reed et al. |
| 6,616,613 B1 | 9/2003 | Goodman |
| 7,194,371 B1 | 3/2007 | McBride et al. |
| 7,317,416 B2 | 1/2008 | Flom et al. |
| 7,421,061 B2 | 9/2008 | Boese et al. |
| 7,647,093 B2 | 1/2010 | Bojovic et al. |
| 7,677,729 B2 | 3/2010 | Vilser et al. |
| 7,691,067 B2 | 4/2010 | Westbrook et al. |

(Continued)

FOREIGN PATENT DOCUMENTS

| | | |
|---|---|---|
| CN | 102660988 | 3/2014 |
| EP | 2417908 | 2/2012 |

(Continued)

OTHER PUBLICATIONS

"Non-Final Office Action", U.S. Appl. No. 14/599,954, Feb. 2, 2016, 17 pages.

(Continued)

*Primary Examiner* — Paula J Stice
(74) *Attorney, Agent, or Firm* — Colby Nipper

(57) ABSTRACT

This document describes assessing cardiovascular function using an optical sensor, such as through sensing relevant hemodynamics understood by pulse transit times, blood pressures, pulse-wave velocities, and, in more breadth, ballistocardiograms and pressure-volume loops. The techniques disclosed in this document use various optical sensors to sense hemodynamics, such as skin color and skin and other organ displacement. These optical sensors require little if any risk to the patient and are simple and easy for the patient to use.

20 Claims, 9 Drawing Sheets

(56) References Cited

U.S. PATENT DOCUMENTS

| | | | |
|---|---|---|---|
| 7,698,154 B2 | 4/2010 | Marchosky | |
| 8,062,220 B2 | 11/2011 | Kurtz et al. | |
| 8,179,604 B1 | 5/2012 | Prada Gomez et al. | |
| 8,289,185 B2 | 10/2012 | Alonso | |
| 8,301,232 B2 | 10/2012 | Albert et al. | |
| 8,475,367 B1 | 7/2013 | Yuen et al. | |
| 8,560,972 B2 | 10/2013 | Wilson | |
| 8,562,526 B2 | 10/2013 | Heneghan et al. | |
| 8,655,004 B2 | 2/2014 | Prest et al. | |
| 8,700,137 B2 | 4/2014 | Albert | |
| 8,758,020 B2 | 6/2014 | Burdea et al. | |
| 8,764,651 B2 | 7/2014 | Tran | |
| 8,790,257 B2 | 7/2014 | Libbus et al. | |
| 8,819,812 B1 | 8/2014 | Weber et al. | |
| 9,230,160 B1 | 1/2016 | Kanter | |
| 9,508,141 B2 | 11/2016 | Khachaturian et al. | |
| 9,594,443 B2 | 3/2017 | Vanblon et al. | |
| 9,600,080 B2 | 3/2017 | Poupyrev | |
| 9,778,749 B2 | 10/2017 | Poupyrev | |
| 2003/0122677 A1 | 7/2003 | Kail | |
| 2004/0249250 A1 | 12/2004 | McGee et al. | |
| 2005/0148876 A1 | 7/2005 | Endoh et al. | |
| 2006/0040739 A1 | 2/2006 | Wells | |
| 2007/0118043 A1 | 5/2007 | Oliver et al. | |
| 2007/0161921 A1 | 7/2007 | Rausch | |
| 2007/0176821 A1 | 8/2007 | Flom et al. | |
| 2007/0197878 A1 | 8/2007 | Shklarski | |
| 2008/0001735 A1 | 1/2008 | Tran | |
| 2008/0039731 A1 | 2/2008 | McCombie et al. | |
| 2008/0065291 A1 | 3/2008 | Breed | |
| 2008/0168396 A1 | 7/2008 | Matas et al. | |
| 2008/0194975 A1 | 8/2008 | MacQuarrie et al. | |
| 2008/0211766 A1 | 9/2008 | Westerman et al. | |
| 2008/0316085 A1 | 12/2008 | Rofougaran et al. | |
| 2008/0320419 A1 | 12/2008 | Matas et al. | |
| 2009/0018408 A1 | 1/2009 | Ouchi et al. | |
| 2009/0058820 A1 | 3/2009 | Hinckley | |
| 2009/0113298 A1 | 4/2009 | Jung et al. | |
| 2009/0115617 A1 | 5/2009 | Sano et al. | |
| 2009/0177068 A1 | 7/2009 | Stivoric et al. | |
| 2009/0270690 A1 | 10/2009 | Roos et al. | |
| 2009/0295712 A1 | 12/2009 | Ritzau | |
| 2010/0094141 A1 | 4/2010 | Puswella | |
| 2010/0179820 A1 | 7/2010 | Harrison et al. | |
| 2010/0204550 A1 | 8/2010 | Heneghan et al. | |
| 2010/0281438 A1 | 11/2010 | Latta et al. | |
| 2010/0292549 A1 | 11/2010 | Schuler | |
| 2010/0306713 A1 | 12/2010 | Geisner et al. | |
| 2010/0324384 A1 | 12/2010 | Moon et al. | |
| 2011/0003664 A1 | 1/2011 | Richard | |
| 2011/0010014 A1 | 1/2011 | Oexman et al. | |
| 2011/0093820 A1 | 4/2011 | Zhang et al. | |
| 2011/0118564 A1 | 5/2011 | Sankai | |
| 2011/0181509 A1 | 7/2011 | Rautiainen et al. | |
| 2011/0197263 A1 | 8/2011 | Stinson, III | |
| 2011/0202404 A1 | 8/2011 | van der Riet | |
| 2011/0213218 A1 | 9/2011 | Weiner et al. | |
| 2011/0221666 A1 | 9/2011 | Newton et al. | |
| 2011/0234492 A1 | 9/2011 | Ajmera et al. | |
| 2011/0239118 A1 | 9/2011 | Yamaoka et al. | |
| 2011/0245688 A1 | 10/2011 | Arora et al. | |
| 2011/0307842 A1 | 12/2011 | Chiang et al. | |
| 2012/0019168 A1 | 1/2012 | Noda et al. | |
| 2012/0029369 A1 | 2/2012 | Icove et al. | |
| 2012/0047468 A1 | 2/2012 | Santos et al. | |
| 2012/0123232 A1 | 5/2012 | Najarian et al. | |
| 2012/0174736 A1 | 7/2012 | Wang et al. | |
| 2012/0220835 A1 | 8/2012 | Chung | |
| 2012/0254810 A1 | 10/2012 | Heck et al. | |
| 2012/0280900 A1 | 11/2012 | Wang et al. | |
| 2012/0310665 A1 | 12/2012 | Xu et al. | |
| 2013/0035563 A1 | 2/2013 | Angelides | |
| 2013/0053653 A1 | 2/2013 | Cuddihy et al. | |
| 2013/0083173 A1 | 4/2013 | Geisner et al. | |
| 2013/0132931 A1 | 5/2013 | Bruns et al. | |
| 2013/0150735 A1 | 6/2013 | Cheng | |
| 2013/0195330 A1 | 8/2013 | Kim et al. | |
| 2013/0278499 A1 | 10/2013 | Anderson | |
| 2013/0278501 A1 | 10/2013 | Bulzacki | |
| 2013/0283203 A1 | 10/2013 | Batraski et al. | |
| 2013/0322729 A1 | 12/2013 | Mestha et al. | |
| 2013/0332438 A1 | 12/2013 | Li et al. | |
| 2013/0345569 A1 | 12/2013 | Mestha et al. | |
| 2014/0005809 A1 | 1/2014 | Frei et al. | |
| 2014/0051941 A1* | 2/2014 | Messerschmidt | A61B 5/6898 600/301 |
| 2014/0072190 A1 | 3/2014 | Wu et al. | |
| 2014/0073486 A1 | 3/2014 | Ahmed et al. | |
| 2014/0073969 A1 | 3/2014 | Zou et al. | |
| 2014/0081100 A1 | 3/2014 | Muhsin et al. | |
| 2014/0095480 A1 | 4/2014 | Marantz et al. | |
| 2014/0121540 A1 | 5/2014 | Raskin | |
| 2014/0135631 A1 | 5/2014 | Brumback et al. | |
| 2014/0139616 A1 | 5/2014 | Pinter et al. | |
| 2014/0143678 A1 | 5/2014 | Mistry et al. | |
| 2014/0191939 A1 | 7/2014 | Penn et al. | |
| 2014/0200416 A1 | 7/2014 | Kashef et al. | |
| 2014/0244277 A1 | 8/2014 | Krishna Rao et al. | |
| 2014/0250515 A1 | 9/2014 | Jakobsson | |
| 2014/0253709 A1 | 9/2014 | Bresch et al. | |
| 2014/0275854 A1 | 9/2014 | Venkatraman et al. | |
| 2014/0280295 A1 | 9/2014 | Kurochikin et al. | |
| 2014/0297006 A1 | 10/2014 | Sadhu | |
| 2014/0306936 A1 | 10/2014 | Dahl et al. | |
| 2014/0316261 A1 | 10/2014 | Lux et al. | |
| 2014/0357369 A1 | 12/2014 | Callens et al. | |
| 2015/0026815 A1 | 1/2015 | Barrett | |
| 2015/0029050 A1 | 1/2015 | Driscoll et al. | |
| 2015/0046183 A1 | 2/2015 | Cireddu | |
| 2015/0077282 A1 | 3/2015 | Mohamadi | |
| 2015/0085060 A1 | 3/2015 | Fish et al. | |
| 2015/0099941 A1 | 4/2015 | Tran | |
| 2015/0100328 A1 | 4/2015 | Kress et al. | |
| 2015/0112606 A1* | 4/2015 | He | G06F 21/00 702/19 |
| 2015/0277569 A1 | 10/2015 | Sprenger et al. | |
| 2015/0287187 A1* | 10/2015 | Redtel | A61B 5/02125 382/128 |
| 2015/0312041 A1 | 10/2015 | Choi | |
| 2015/0346820 A1 | 12/2015 | Poupyrev et al. | |
| 2015/0351703 A1 | 12/2015 | Phillips et al. | |
| 2016/0041617 A1 | 2/2016 | Poupyrev | |
| 2016/0041618 A1 | 2/2016 | Poupyrev | |
| 2016/0054792 A1 | 2/2016 | Poupyrev | |
| 2016/0054803 A1 | 2/2016 | Poupyrev | |
| 2016/0054804 A1 | 2/2016 | Gollakata et al. | |
| 2016/0055201 A1 | 2/2016 | Poupyrev et al. | |
| 2016/0098089 A1 | 4/2016 | Poupyrev | |
| 2016/0100166 A1 | 4/2016 | Dragne et al. | |
| 2016/0106328 A1* | 4/2016 | Mestha | A61B 5/7282 600/480 |
| 2016/0206244 A1 | 7/2016 | Rogers | |
| 2016/0213331 A1 | 7/2016 | Gil et al. | |
| 2016/0220152 A1 | 8/2016 | Meriheinä et al. | |
| 2016/0321428 A1 | 11/2016 | Rogers | |
| 2016/0338599 A1 | 11/2016 | DeBusschere et al. | |

FOREIGN PATENT DOCUMENTS

| | | |
|---|---|---|
| FR | 3017722 | 8/2015 |
| JP | 113860 | 4/1999 |
| WO | WO-9001895 | 3/1990 |
| WO | WO-0127855 | 4/2001 |
| WO | WO-02082999 | 10/2002 |
| WO | 2004004557 | 1/2004 |
| WO | WO-2009032073 | 3/2009 |
| WO | WO-2013186696 | 12/2013 |
| WO | WO-2013191657 | 12/2013 |
| WO | WO-2013192166 | 12/2013 |
| WO | WO-2014116968 | 7/2014 |
| WO | WO-2014124520 | 8/2014 |
| WO | WO-2014136027 | 9/2014 |
| WO | WO-2014138280 | 9/2014 |

(56) References Cited

FOREIGN PATENT DOCUMENTS

| WO | WO-2014160893 | 10/2014 |
|---|---|---|
| WO | 2016118534 | 7/2016 |
| WO | 2016176471 | 11/2016 |
| WO | 2016178797 | 11/2016 |
| WO | 2017019299 | 2/2017 |

OTHER PUBLICATIONS

"Non-Final Office Action", U.S. Appl. No. 14/504,038, Feb. 26, 2016, 22 pages.
"Philips Vital Signs Camera", Retrieved From: <http://www.vitalsignscamera.com/> Apr. 15, 2015, Jul. 17, 2013, 2 pages.
"Cardiio", Retrieved From: <http://www.cardiio.com/> Apr. 15, 2015 App Information Retrieved From: <https://itunes.apple.com/us/app/cardiio-touchless-camera-pulse/id542891434?ls=1&mt=8> Apr. 15, 2015, Feb. 24, 2015, 6 pages.
Balakrishnan,"Detecting Pulse from Head Motions in Video", In Proceedings: CVPR '13 Proceedings of the 2013 IEEE Conference on Computer Vision and Pattern Recognition Available at: <http://people.csail.mit.edu/mrub/vidmag/papers/Balakrishnan_Detecting_Pulse_from_2013_CVPR_paper.pdf>, Jun. 23, 2013, 8 pages.
Couderc,"Detection of Atrial Fibrillation using Contactless Facial Video Monitoring", In Proceedings: Heart Rhythm Society, vol. 12, Issue 1 Available at: <http://www.heartrhythmjournal.com/article/S1547-5271(14)00924-2/pdf>, Jan. 2015, 7 pages.
Poh,"A Medical Mirror for Non-contact Health Monitoring", In Proceedings: ACM SIGGRAPH Emerging Technologies Available at: <http://affect.media.mit.edu/pdfs/11.Poh-etal-SIGGRAPH.pdf>, 2011, 1 page.
Poh,"Non-contact, Automated Cardiac Pulse Measurements Using Video Imaging and Blind Source Separation.", In Proceedings: Optics Express, vol. 18, No. 10 Available at: <http://www.opticsinfobase.org/view_article.cfm?gotourl=http%3A%2F%2Fwww%2Eopticsinfobase%2Eorg%2FDirectPDFAccess%2F77B04D55%2DBC95%2D6937%2D5BAC49A426378C02%5F199381%2Foe%2D18%2D10%2D10762%2Ep, May 7, 2010, 13 pages.
Wang,"Exploiting Spatial Redundancy of Image Sensor for Motion Robust rPPG", In Proceedings: IEEE Transactions on Biomedical Engineering, vol. 62, Issue 2, Jan. 19, 2015, 11 pages.
He,"A Continuous, Wearable, and Wireless Heart Monitor Using Head Ballistocardiogram (BCG) and Head Electrocardiogram (ECG) with a Nanowatt ECG Heartbeat Detection Circuit", In Proceedings: Thesis, Department of Electrical Engineering and Computer Science, Massachusetts Institute of Technology Available at: <http://dspace.mit.edu/handle/1721.1/79221>, Feb. 2013, 137 pages.
Nakajima,"Development of Real-Time Image Sequence Analysis for Evaluating Posture Change and Respiratory Rate of a Subject in Bed", In Proceedings: Physiological Measurement, vol. 22, No. 3, Retrieved From: <http://iopscience.iop.org/0967-3334/22/3/401/pdf/0967-3334_22_3_401.pdf> Feb. 27, 2015, Aug. 2001, 8 pages.
"Final Office Action", U.S. Appl. No. 14/504,038, Sep. 27, 2016, 23 pages.
"Final Office Action", U.S. Appl. No. 14/599,954, Aug. 10, 2016, 23 pages.
"International Search Report and Written Opinion", Application No. PCT/US2016/032307, Aug. 25, 2016, 13 pages.
"International Search Report and Written Opinion", Application No. PCT/US2016/029820, Jul. 15, 2016, 14 pages.
"Non-Final Office Action", U.S. Appl. No. 14/518,863, Oct. 14, 2016, 16 pages.
"Non-Final Office Action", U.S. Appl. No. 14/582,896, Jun. 29, 2016, 9 pages.
"Non-Final Office Action", U.S. Appl. No. 14/666,155, Aug. 24, 2016, 9 pages.
"Notice of Allowance", U.S. Appl. No. 14/582,896, Nov. 7, 2016, 5 pages.
"Pre-Interview Communication", U.S. Appl. No. 14/513,875, Oct. 21, 2016, 3 pages.
"Restriction Requirement", U.S. Appl. No. 14/666,155, Jul. 22, 2016, 5 pages.
"The Instant Blood Pressure app estimates blood pressure with your smartphone and our algorithm", Retrieved at: http://www.instantbloodpressure.com/—on Jun. 23, 2016, 6 pages.
Espina,"Wireless Body Sensor Network for Continuous Cuff-less Blood Pressure Monitoring", International Summer School on Medical Devices and Biosensors, 2006, Sep. 2006, 5 pages.
Klabunde,"Ventricular Pressure-Volume Loop Changes in Valve Disease", Retrieved From <https://web.archive.org/web/20101201185256/http://cvphysiology.com/Heart%20Disease/HD009.htm>, Dec. 1, 2010, 8 pages.
"Corrected Notice of Allowance", U.S. Appl. No. 14/582,896, Dec. 19, 2016, 2 pages.
"International Search Report and Written Opinion", Application No. PCT/US2016/042013, Oct. 26, 2016, 12 pages.
"International Search Report and Written Opinion", Application No. PCT/US2016/033342, Oct. 27, 2016, 20 pages.
"Non-Final Office Action", U.S. Appl. No. 14/504,121, Jan. 9, 2017, 13 pages.
Matthews,"Venous Pulse", Retrieved at: http://www.rjmatthewsmd.com/Definitions/venous_pulse.htm—on Nov. 30, 2016, Apr. 13, 2013, 7 pages.
"Corrected Notice of Allowance", U.S. Appl. No. 14/582,896, Feb. 6, 2017, 2 pages.
"Corrected Notice of Allowance", U.S. Appl. No. 14/582,896, Feb. 23, 2017, 2 pages.
"Final Office Action", U.S. Appl. No. 14/518,863, May 5, 2017, 18 pages.
"International Preliminary Report on Patentability", Application No. PCT/US2015/043963, Feb. 16, 2017, 12 pages.
"International Preliminary Report on Patentability", Application No. PCT/US2015/043949, Feb. 16, 2017, 13 pages.
"Life:X Lifestyle eXplorer", Retrieved from <https://web.archive.org/web/20150318093841/http://research.microsoft.com/en-us/projects/lifex >, Feb. 3, 2017, 2 pages.
"Non-Final Office Action", U.S. Appl. No. 14/504,038, Mar. 22, 2017, 33 pages.
"Non-Final Office Action", U.S. Appl. No. 14/513,875, Feb. 21, 2017, 9 pages.
"Non-Final Office Action", U.S. Appl. No. 14/599,954, Jan. 26, 2017, 16 pages.
"Non-Final Office Action", U.S. Appl. No. 14/666,155, Feb. 3, 2017, 12 pages.
"Pre-Interview Communication", U.S. Appl. No. 14/494,863, Jan. 27, 2017, 5 pages.
"Pre-Interview Communication", U.S. Appl. No. 14/715,454, Apr. 14, 2017, 3 pages.
"Pre-Interview Communication", U.S. Appl. No. 14/715,793, Mar. 20, 2017, 3 pages.
"The Dash smart earbuds play back music, and monitor your workout", Retrieved from <http://newatlas.com/bragi-dash-tracking-earbuds/30808/>, Feb. 13, 2014, 3 pages.
Palese, "The Effects of Earphones and Music on the Temperature Measured by Infrared Tympanic Thermometer: Preliminary Results", ORL—head and neck nursing: official journal of the Society of Otorhinolaryngology and Head-Neck Nurses 32.2, 2013, pp. 8-12.
Tympanic Thermometer: Preliminary Results, ORL—head and neck nursing: official journal of the Society of Otorhinolaryngology and Head-Neck Nurses 32.2, 2013, pp. 8-12.
"Clever Toilet Checks on Your Health", CNN.Com; Technology, Jun. 28, 2005, 2 pages.
"Final Office Action", U.S. Appl. No. 14/504,121, dated Aug. 8, 2017, 16 pages.
"First Action Interview OA", U.S. Appl. No. 14/715,793, dated Jun. 21, 2017, 3 pages.
"First Action Interview Pilot Program Pre-Interview Communication", U.S. Appl. No. 14/731,195, dated Aug. 1, 2017, 3 pages.

(56) References Cited

OTHER PUBLICATIONS

"Non-Final Office Action", U.S. Appl. No. 14/720,632, dated Jun. 14, 2017, 16 pages.
"Notice of Allowance", U.S. Appl. No. 14/513,875, dated Jun. 28, 2017, 7 pages.
"Notice of Allowance", U.S. Appl. No. 14/666,155, dated Jul. 10, 2017, 7 pages.
"Notice of Allowance", U.S. Appl. No. 14/504,038, dated Aug. 7, 2017, 17 pages.
"Notice of Allowance", U.S. Appl. No. 14/599,954, dated May 24, 2017, 11 pages.
"Notice of Allowance", U.S. Appl. No. 14/494,863, dated May 30, 2017, 7 pages.
Otto, et al., "System Architecture of a Wireless Body Area Sensor Network for Ubiquitous Health Monitoring", Journal of Mobile Multimedia; vol. 1, No. 4, Jan. 10, 2006, 20 pages.
"Apple Watch Used Four Sensors to Detect your Pulse", retrieved from http://www.theverge.com/2014/9/9/6126991/US2016/026756 on Nov. 10, 2017, The Verge, paragraph 1, Sep. 9, 2014, 4 pages.
"Final Office Action", U.S. Appl. No. 14/715,454, dated Sep. 7, 2017, 14 pages.
"Final Office Action", U.S. Appl. No. 14/715,793, dated Sep. 12, 2017, 7 pages.
"Non-Invasive Quantification of Peripheral Arterial Volume Distensibility and its Non-Linear Relationship with Arterial Pressure", Journal of Biomechanics, Pergamon Press, vol. 42, No. 8; as cited in the search report for PCT/US2016/013968 citing the whole document, but in particular the abstract, May 29, 2009, 2 pages.
"Pressure-Volume Loop Analysis in Cardiology", retrieved from https://en.wikipedia.org/w/index.php?title=Pressure-volume loop analysis in card iology&oldid=636928657 on Sep. 23, 2017; Obtained per link provided in search report from PCT/US2016/01398 on Jul. 28, 2016, Dec. 6, 2014, 10 pages.
"Written Opinion", PCT Application No. PCT/US2016/042013, dated Feb. 2, 2017, 6 pages.
"Written Opinion", PCT Application PCT/US2016/013968, dated Jul. 28, 2016, 9 pages.
"Written Opinion", PCT Application No. PCT/US2016/026756, dated Nov. 10, 2016, 7 pages.
Ishijima, "Unobtrusive Approaches to Monitoring Vital Signs at Home", Medical & Biological Engineering and Computing, Springer, Berlin, DE, vol. 45, No. 11 as cited in search report for PCT/US2016/013968 on Jul. 28, 2016, Sep. 26, 2007, 3 pages.
"International Preliminary Report on Patentability", PCT Application No. PCT/US2016/026756, dated Oct. 19, 2017, 8 pages.
"Non-Final Office Action", U.S. Appl. No. 14/518,863, dated Sep. 29, 2017, 20 pages.
"Non-Final Office Action", U.S. Appl. No. 14/699,181, dated Oct. 18, 2017, 33 pages.

* cited by examiner

US 9,848,780 B1

ASSESSING CARDIOVASCULAR FUNCTION USING AN OPTICAL SENSOR

BACKGROUND

Cardiovascular disease is the leading cause of morbidity and mortality worldwide. At the same time this chronic disease is largely preventable. Medical science knows how to save most of these lives by removing the major risk factors of smoking, diabetes, and hypertension. And many people are told just what they need to do to reduce these risk factors—stop smoking, reduce sugar intake, eat healthier, reduce alcohol intake, increase cardiovascular exercise, lose weight, and, if needed, take blood-pressure medication. But many people do not follow this good advice. Because of this, millions of people needlessly die from cardiovascular disease.

People don't follow this good medical advice because they think they are different, they do not want to change their behaviors that are causing the disease, or they do not know what to change in their particular case. When a physician tells them that they are at risk from heart disease because they are overweight, for example, many people know that this judgment is not necessarily specific to them—it is based on averages and demographics. So being a particular weight may not negatively affect a particular patient's heart. Further, a lack of feedback that their behavior is harming their heart results in a lack of incentive for them to change their behavior.

This lack of incentive to follow good advice can be addressed by monitoring the state of the patient's cardiovascular system over time to show trends in heart health. Hard data often motivates patients to modify their behavior, such as data indicating that their heart shows measurable signs of heart disease. Unfortunately, current methods for measuring heart health can be inconvenient, stressful, and expensive. Simple home monitor products exist for measuring heart rate and blood pressure, but long-term user compliance is a problem due to inconvenience. More advanced cardiovascular monitoring, such as heart rate variability, arterial stiffness, cardiac output, and atrial fibrillation, involve expensive and time-consuming trips to a medical facility for a skilled assessment. Because of this, only patients that demonstrate late stage symptoms of heart disease are likely to receive these tests, which is generally too late to make simple lifestyle changes that would avoid a chronic disease.

Another reason that people don't follow this good advice, or don't follow it for long enough to prevent heart disease, is because they do not see the benefit. When people take the advice of changing their diet and habits—which most people do not want to do—they often don't see the improvement before they lose the motivation to continue monitoring their cardiovascular status. Because of this, many people go back to their old habits only to later die of heart disease.

SUMMARY

This document describes assessing cardiovascular function using an optical sensor, such as through sensing relevant hemodynamics understood by heart and respiration rates, heart rate variability, blood pressures, pulse-wave velocities, arterial stiffness, cardiac valve timing, ballistocardiogram force, photo-plethysmograms, blood oxygenation, and pressure-volume loops. The techniques disclosed in this document use various optical sensors to sense the effects of cardiovascular hemodynamics, such as skin color or displacement at multiple spatial locations on the body. These optical sensors require little if any risk to the patient and are simple and easy for the patient to use.

Further, the techniques described herein can determine blood flow asymmetries, which may indicate a stroke or other cardiovascular disease or pressure waveforms, which may indicate cardiac abnormalities, such as atrial fibrillation. These techniques may also determine trends in a patient's cardiovascular health. These trends can aid a patient by helping them know if the effort they are expending to improve their heart health is actually making a difference. Further, negative trends or conditions, such as cardiac irregularities or some asymmetries can be found that can spur people to improve their health or to get medical attention. By so doing, these techniques may save many people from dying of heart disease.

This summary is provided to introduce simplified concepts concerning the techniques, which are further described below in the Detailed Description. This summary is not intended to identify essential features of the claimed subject matter, nor is it intended for use in determining the scope of the claimed subject matter.

BRIEF DESCRIPTION OF THE DRAWINGS

Embodiments of techniques and devices for assessing cardiovascular function using an optical sensor are described with reference to the following drawings. The same numbers are used throughout the drawings to reference like features and components.

DETAILED DESCRIPTION

Overview

Figure 1:
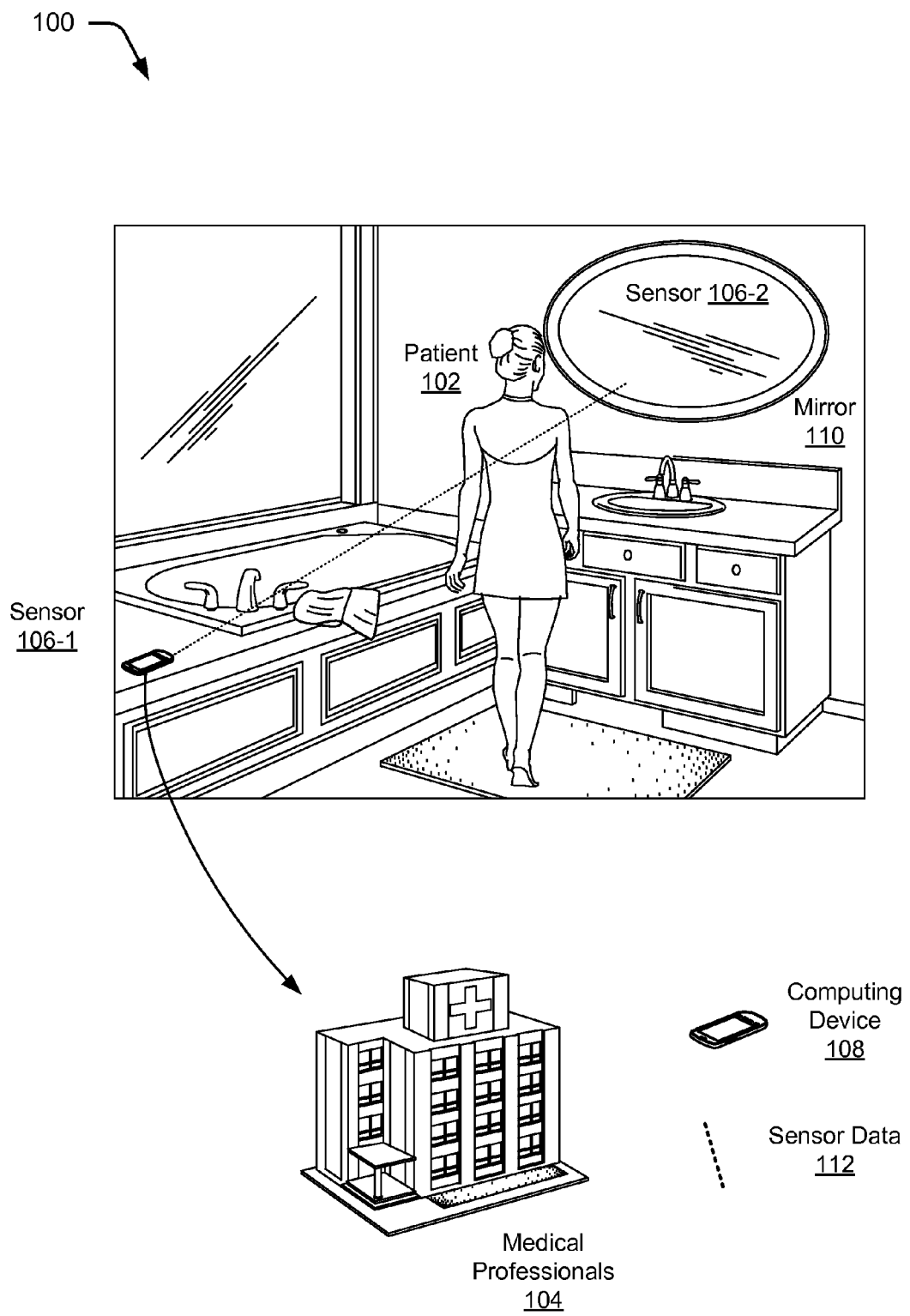
FIG. 1 illustrates an example environment in which the techniques can be implemented.

This document describes techniques using, and devices enabling, assessment of cardiovascular function using an optical sensor. Through use of optical sensors a patient's skin color and displacement over time can be accurately measured, including by comparing colors and displacements at different regions of the patient. For example, an optical sensor can measure a color change at a patient's cheek and, based on that color change, the techniques can determine that the patient's heart beat has produced a peak blood-pressure flow at some particular instant at the cheek. Another optical sensor can measure a color change or displacement at the patient's wrist for the same heartbeat, which the techniques can determine indicates a peak blood-pressure flow at the wrist at some other instant. By comparing the times and distance between these regions, a pulse-wave velocity can be assessed. This pulse-wave velocity can then be used to determine arterial stiffness, blood pressure, and other measurements of cardiovascular function. Simultaneously, those two measurement points can be used to independently measure other vitals like heart rate and respiration rate, with the combination of the two used to improve the measurement by compensating for movements, illumination changes, or occlusions.

In addition to assessing cardiovascular heath at some snapshot in time, the techniques may also measure trends in cardiovascular function. By way of one example, assume that a patient has an optical sensor in her bathroom that is capable of measuring color and displacement at multiple regions, such as her neck, palm, and forehead. This optical sensor measures skin color variations between or within a region, which can indicate differential blood volume to provide a photo-plethysmogram (PPG). If the patient has other optical sensors, such as one in her computing spectacles and another in her smartphone, these can further aid the accuracy and robustness of the measurements. Using these sensors, assume that over the course of a new diet and exercise routine that the techniques, using data from the optical sensors, determine that her heart's stroke volume (an important measure of heart health) has improved 6% in four weeks. With this positive feedback, this patient may continue her diet and exercise routine, thereby likely reducing the chances that she will die of heart disease.

For another case, assume that the techniques determine that there is an asymmetry in blood flow within a patient's face. This asymmetry can be indicated to the patient or a medical professional sufficient to perform further testing, as asymmetry can indicate a stroke (a deadly disease that, with a fast diagnosis and treatment can save the patient's life or quality of life) or other vascular disease.

These are but a few examples in which assessing cardiovascular function using an optical sensor can be performed, other examples and details are provided below. This document now turns to an example environment, after which example optical sensors and methods, cardiovascular functions and trends, and an example computing system are described.

Example Environment

FIG. 1 is an illustration of an example environment 100 in which assessing cardiovascular function using an optical sensor can be employed. Environment 100 illustrates a patient 102 that is a subject of the health monitoring, as well as a medical professional 104, family member, or other caretaker that, in some cases, will receive results of the health monitoring. This example employs optical sensors 106, a color and displacement optical sensor 106-1 (sensor 106-1), which is part of computing device 108, and a hyperspectral sensor 106-2 (sensor 106-2), which is located within mirror 110.

Sensor data 112 is provided by each of optical sensors 106 to some computing device. As shown, sensor data 112 is passed from sensor 106-2 to computing device 108 while sensor 106-1 is integral with computing device 108 and need not be passed if the techniques are performed at that device. Computing device 108 then performs some or all of the techniques, or passes that sensor data to some other computing device, such as a remote server through a communication network (not shown).

As shown with this example environment 100, a sensing milieu (e.g., optical sensors 106 in patient 102's bathroom) in which a patient lives can be used that are capable of determining a cardiovascular function of a human cardiovascular system. This sensing milieu is capable of non-invasively and remotely determining this cardiovascular function and trends in this cardiovascular function. This sensing milieu senses various regions of the patient, which can then be compared, time correlated, aggregated, averaged, and so forth to determine a cardiovascular function. These cardiovascular functions can be represented by cardiovascular asymmetries (e.g., due to a stoke), cardiac irregularities (e.g. atrial fibrillation), blood pressure, pulse-wave velocity, waveforms of circulating blood, photo-plethysmograms (PPG), ballistocardiograms, and pressure-volume loops, to name a few.

Figure 2:
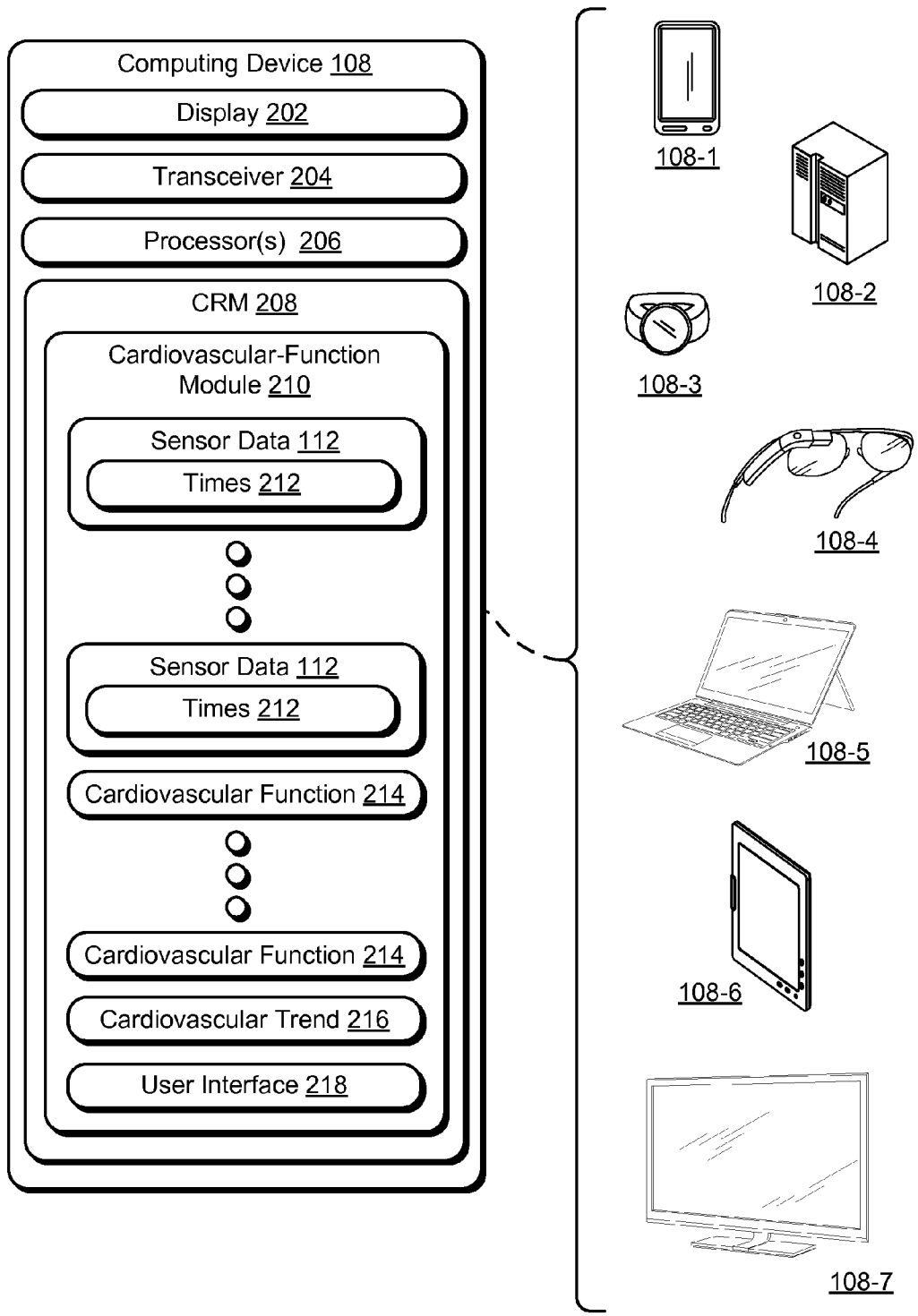
FIG. 2 illustrates an example computing device of FIG. 1.

With regard to the example computing device 108 of FIG. 1, consider a detailed illustration in FIG. 2. Computing device 108 can be one or a combination of various devices, here illustrated with seven examples: a smartphone 108-1, a server 108-2, a computing watch 108-3, computing spectacles 108-4, a laptop 108-5, a tablet computer 108-6, and a desktop 108-7, though other computing devices and systems, such as a netbook or set-top box may also be used. As noted above, in some embodiments the techniques operate, in whole or in part, through a remote device such as server 108-2. In such cases, some computing can be forgone locally, e.g., through a communication device having limited computing operations or even directly from optical sensors 106 to server 108-2.

Computing device 108 includes or is able to communicate with a display 202 (six are shown in FIG. 2), a transceiver 204, one or more processors 206, and computer-readable storage media 208 (CRM 208). Transceiver 204 is capable of sending and receiving data directly or through a communication network, such as sensor data 112 from optical sensors 106 through a local area, wide area, functional area, cellular, or near-field network.

CRM 208 includes cardiovascular-function module 210, which includes or has access to sensor data 112 from one or more of multiple optical sensors 106. This sensor data 112 can be associated with particular times 212, such that simultaneously received sensor data 112 can be correlated to determine cardiovascular functions 214 of human cardiovascular systems and trends 216 can be determined based on sensor data 112 changing over time. CRM 208 also includes or has access to a user interface 218, that, while not required, can be used to present determined trends, health, and medical advice to patient 102.

Generally, cardiovascular-function module 210 is capable of determining, based on sensor data 112, a cardiovascular function of a cardiovascular system of a patient, such as patient 102 of FIG. 1. With this cardiovascular function, cardiovascular-function module 210 may alert patient 102 or medical professionals 104 or family members/caretakers of a negative health condition needing immediate care, for example. Medical professional 104, or a specialized machine intelligence, could schedule an in-person appointment or remotely adjust patient care through changes in medication or lifestyle. Cardiovascular-function module 210 is also configured to determine trends based on the current cardiovascular function and prior-determined cardiovascular functions, such as those determined at prior times.

More specifically, cardiovascular-function module 210 is capable of receiving and using optical sensor data indicating a skin, organ, or structure's color or displacement. This data may come from single or multiple optical sensors covering the same or different wavelengths observing multiple locations on the patient's body. With this data, cardiovascular-function module 210 can determine timing relationships, pulse pressure waveforms, and asymmetries in a patient's cardiovascular system. With this data and a circulatory distance between data from different regions of the patient, as well as time correlations between the data, cardiovascular-function module 210 can determine a pulse-wave velocity and various simple or highly sophisticated measures of cardiovascular function, including charts of blood pressure, a ballistocardiogram, a photo-plethysmogram (PPG), and pressure-volume loops. Capabilities of cardiovascular-function module 210 are addressed further in methods described below.

Figure 3:
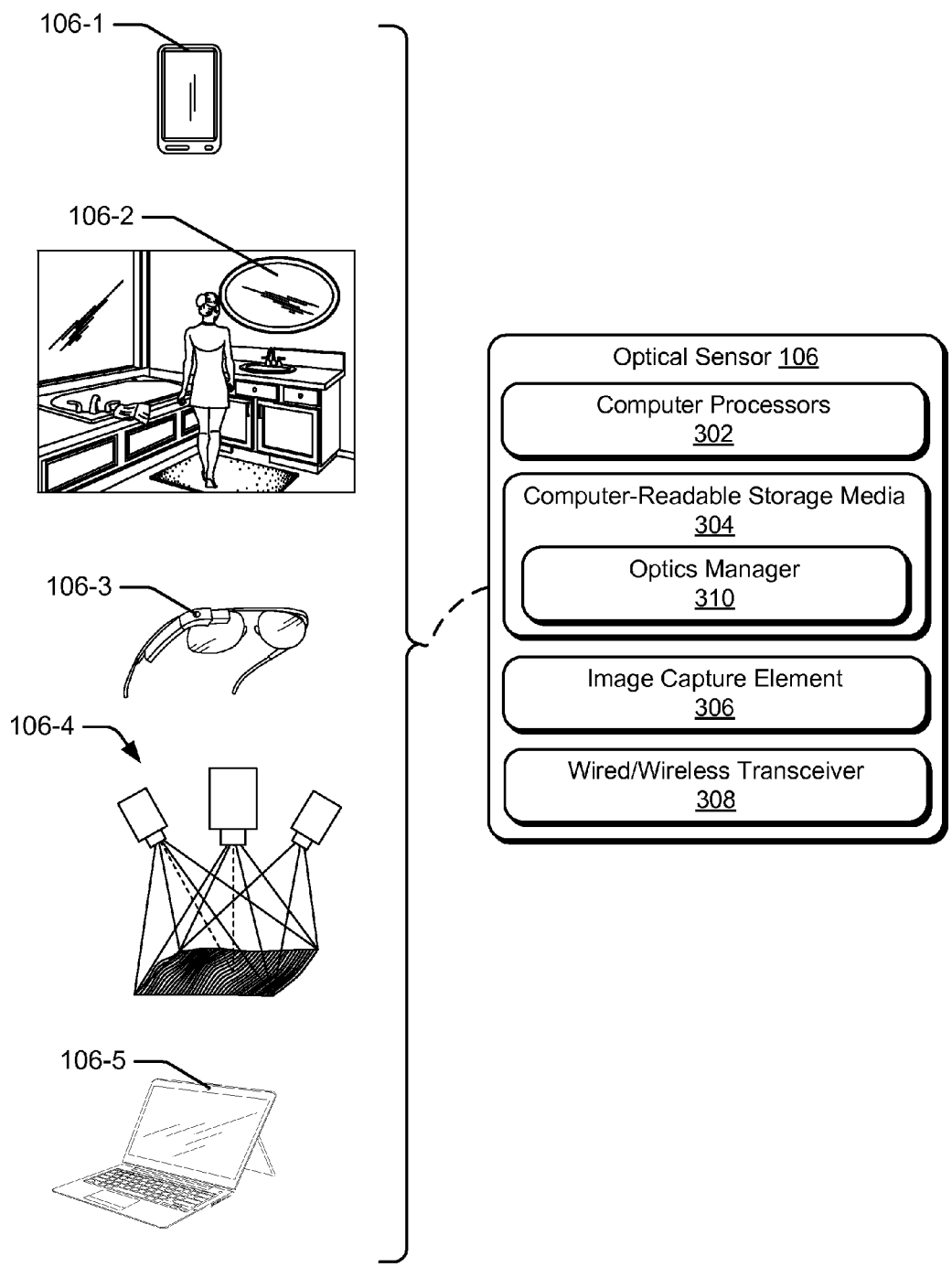
FIG. 3 illustrates an example optical sensor of FIG. 1.

With regard to optical sensors 106, two examples of which are shown in FIG. 1, consider a detailed illustration in FIG. 3. Generally, optical sensors 106 are capable of detecting blood volume, color, and/or displacement at one or more regions of a patient. Optical sensors 106 may include a standard RGB (red, green, blue) sensor, a monochrome sensor, a hyperspectral sensor, a stereoscopic sensor, a structured light sensor, or combinations of multiple sensors, along with a combination of illumination sources such as uniform, infrared, tangential, modulated/coded, or coherent (laser). Optical sensors 106 may also have a fixed camera position or consist of one or more cameras and light sources on mechanical targeting platforms or those that simply move due to being part of a mobile device. Optical sensors 106 may also be separated into physically and spatially distinct devices capable of monitoring the body from multiple view angles or observing different regions of the body. Thus, one of optical sensors 106 may capture an image indicating blood volume at two different regions of patient 102, which then can be compared, by cardiovascular-function module 210, to determine a blood-volume asymmetry or other cardiac function. In the case of a blood-volume asymmetry, a difference in vascular function between the regions may indicate a cardiac-related health problem, such as a stroke. Optical sensors 106 provide various types of information, and are not limited to determining asymmetries.

In more detail, optical sensor 106 can be one or a combination of various devices, here illustrated with color and displacement optical sensor 106-1 (e.g., a camera of computing device 108), sensor 106-2, which is stationary and located within mirror 110, a wearable color and displacement optical sensor 106-3, which is part of computing spectacles 108-4, structured-light or stereoscopic sensor system 106-4, and optic sensor 106-5 of laptop 108-5. The cameras can also be motorized to accurately point at specific points on the body.

As noted in part, sensor 106-2 is capable of capturing images in an ultraviolet, visible, or infrared optical wavelength. Images recording these wavelengths can be used to determine various changes in blood movement or as calibration signals to detect changes in illumination or patient movement. In some cases blood perfusion and oxygen content can be ascertained, thereby further enabling robust measurement of cardiac function. Due to differential wavelength absorption between human tissue and blood, a hyperspectral sensor can also be used to penetrate the skin to map out veins and arteries to target closer examination for displacement and other measurements.

Structured-light sensor system 106-4 is capable of projecting structured light at patient 102 and sensing, often with two or more optical sensors, the projected structured light on patient 102 effective to enable capture of images having surface information. This surface information can be used to calculate depth and surface changes for a region of patient 102, such as skin, another organ, or other structure. These changes can be highly accurate, thereby indicating small vibrations and other changes in an organ or structure caused by the cardiovascular system, and thus how that system is operating. Structured-light sensor system 106-4 can, alternatively, be replaced with or supplemented with a targeted, coherent light source for more-accurate displacement measurements. This may include LIDAR (e.g., "light radar" or the process measuring distance by illuminating a target with a laser and analyzing light reflected from the target), laser interferometry, or a process of analyzing light speckle patterns produced by a coherent light on a skin's surface through optical tracking, which enables detection of very small skin displacements.

These optical sensors 106 can capture images with sufficient resolution and at sufficient shutter speeds to show detailed colors and displacement, and thus enable determination of mechanical movements or vibrations. These mechanical movements and mechanical vibrations are sufficient to determine a ballistocardiogram (BCG) showing patient 102's cardiac function. Other sensing manners, such as color change or skin displacement in a different region of a patient's body, can be used to establish motion frequency bands to amplify, as well as a timing reference for aggregating multiple heartbeat measurements to improve accuracy of a BCG motion. This BCG information can also be used to provide reference timing information about when a blood pressure pulse leaves the left ventricle and enters the aorta, which combined with the other measurements across the body allows for more-precise estimates of pulse transit times and pulse-wave velocities.

While the BCG signal indicates the timing of the aortic valve, the timing of the atrial valve can be monitored by tracking atrial pressure waveforms visible in the external or internal jugular. This also allows for the opportunity to detect atrial fibrillation by detecting missing atrial-pressure pulses. Additionally, aortic-wall stiffness has proven prognostic value in predicting cardiovascular morbidity and mortality. Measuring the pulse-transit time from the start of ejection from the left ventricle into the aorta and up the carotid allows an estimate of that aortic stiffness as well as trending of changes in that stiffness. Thus, determination of arterial-wall stiffness can made independent of blood pressure measurements.

In more detail, optical sensors 106 are configured to capture sufficient information for the techniques to determine blood asymmetries and other cardiac function, including a pulse-wave velocity of patient 102's blood. This pulse-wave velocity is a measure of a patient's arterial health. In healthy arteries the pulse-wave velocity is low due to the elasticity of the arteries but, as they harden and narrow, the pulse-wave velocity rises. Additionally, as blood pressure increases and dilates the arteries, the walls become stiffer, increasing the pulse-wave velocity. While a particular pulse-wave velocity as a snapshot in time may or may not accurately indicate cardiovascular health (e.g., a one-time test at a doctor's office), a change in this pulse-wave velocity (that is, a trend), can be an accurate measure of a change in patient 102's cardiovascular health. If a positive trend, this can reinforce patient 102's healthy habits and, if negative, encourage changes to be made.

In more detail, each of the color-sensing optical sensors 106 is configured to record colors in a patient's skin sufficient to determine a photo-plethysmogram. This PPG measures variations in a size or color of an organ, limb, or other human part from changes in an amount of blood present in or passing through it. These colors and color variations in a patient's skin can show heart rate and efficiency.

These examples show some ways in which the techniques can provide substantially more-valuable (or at least different) data by which to assess a patient's cardiac function than those provided in a medical office or hospital. As noted, conventional health monitoring is often performed at a hospital or medical practitioner's office. Health monitoring at a hospital or office, however, cannot monitor a patient during their normal course of life or as often as desired. This can be a serious limitation because a snapshot captured at a hospital or office may not accurately reflect the patient's health or may not performed at all due to the infrequency of a patient's visits. Even if testing at a hospital or medical office is performed often, it can be inaccurate due to it being of a short duration or due to the testing being in an artificial environment. Note that this does not preclude the use of the techniques disclosed herein at a hospital or medical office, where they may prove valuable in supplementing or replacing conventional measurements, and in the case of in-patient care, may provide a manner for continuous monitoring of patients that are critically (or otherwise) ill.

Returning to FIG. 3, optical sensor 106 generally may have various computing capabilities, though it may instead be a low-capability device having little or no computing capability. Here optical sensor 106 includes one or more computer processors 302, computer-readable storage media 304, image capture element 306, and a wired or wireless transceiver 308 capable of receiving and transmitting information (e.g., to computing device 108). Image capture element 306 may include simple or complex cameras, such as those having low or high shutter speeds, low or high frame rates, low or high resolutions, and having or not having non-visible imaging capabilities. Computer-readable storage media 304 includes optics manager 310, which is capable of processing sensor data and recording and transmitting sensor data, as well as receive or assign appropriate time markers by which to mark or compare the time of various captured images. Optics manager 310 and cardiovascular-function module 210 may also calibrate image capture element 306 through use of an external sensor. This can aid in calibrating skin colors or displacements to a calibration color or displacement, or even to a cardiac function, such as to a blood pressure or pulse-wave velocity. Thus, while one of optical sensors 106 captures images for two regions, a blood pressure between those regions is also measured through a different device, thereby enabling more-accurate determination of cardiac functions for the optical sensor and for that patient. Other potential calibration sensors include, but are not limited to, ECG, conventional BCG, digital stethoscopes, ultrasound, and the like. Another example is the use of an external blood pressure meter to calibrate the pulse wave velocity over time to determine long-term changes in arterial-wall stiffness by separating arterial stiffness due to blood pressure versus that due to the dilation by blood pressure.

These and other capabilities, as well as ways in which entities of FIGS. 1-3 act and interact, are set forth in greater detail below. These entities may be further divided, combined, and so on. The environment 100 of FIG. 1 and the detailed illustrations of FIGS. 2 and 3 illustrate some of many possible environments capable of employing the described techniques.

Example Methods

Figure 4:
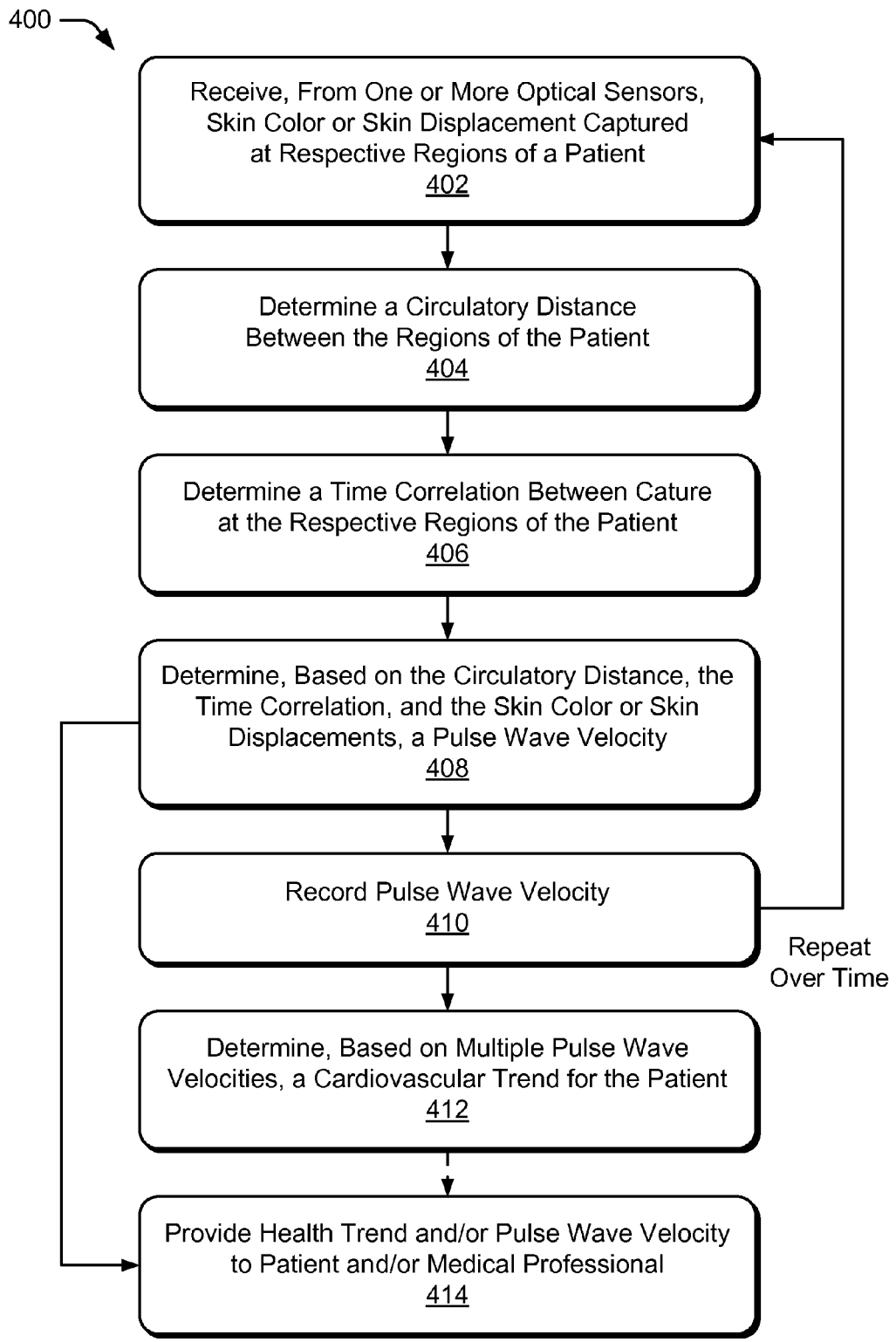
FIG. 4 illustrates a method for assessing cardiovascular function using an optical sensor, including determination of a pulse-wave velocity for a patient.
Figure 8:
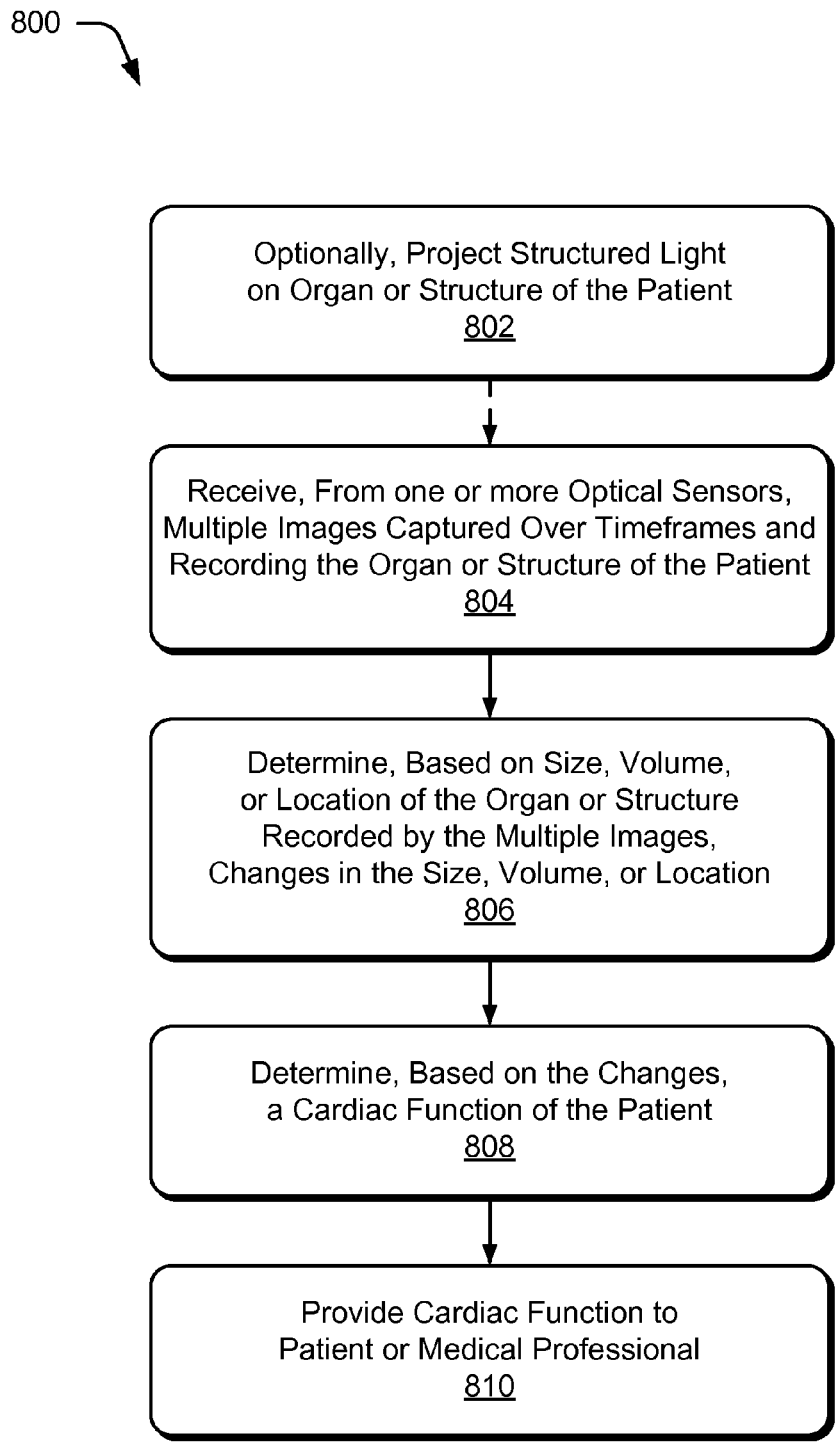
FIG. 8 illustrates a method for assessing cardiovascular function using an optical sensor based on size, volume, or location of an organ or structure of a patient.

FIGS. 4 and 8 depict methods that assess cardiovascular function using an optical sensor. These methods are shown as sets of blocks that specify operations performed but are not necessarily limited to the order or combinations shown for performing the operations by the respective blocks. In portions of the following discussion reference may be made to environment 100 of FIG. 1 and entities detailed in FIGS. 2 and 3, reference to which is made for example only. The techniques are not limited to performance by one entity or multiple entities operating on one device.

At 402, skin colors or skin displacements are received from one or more optical sensors. These skin colors or displacements are captured at regions of a patient, such as a color captured at a patient's skin on her forehead and a displacement of skin on her neck or on her clavicle. Optionally, as part of operation 402, cardiovascular-function module 210 or optics manager 310 may automatically determine which regions of a patient are fully visible or partially occluded, and thereby determine better regions of a patient to capture images.

Figure 5:
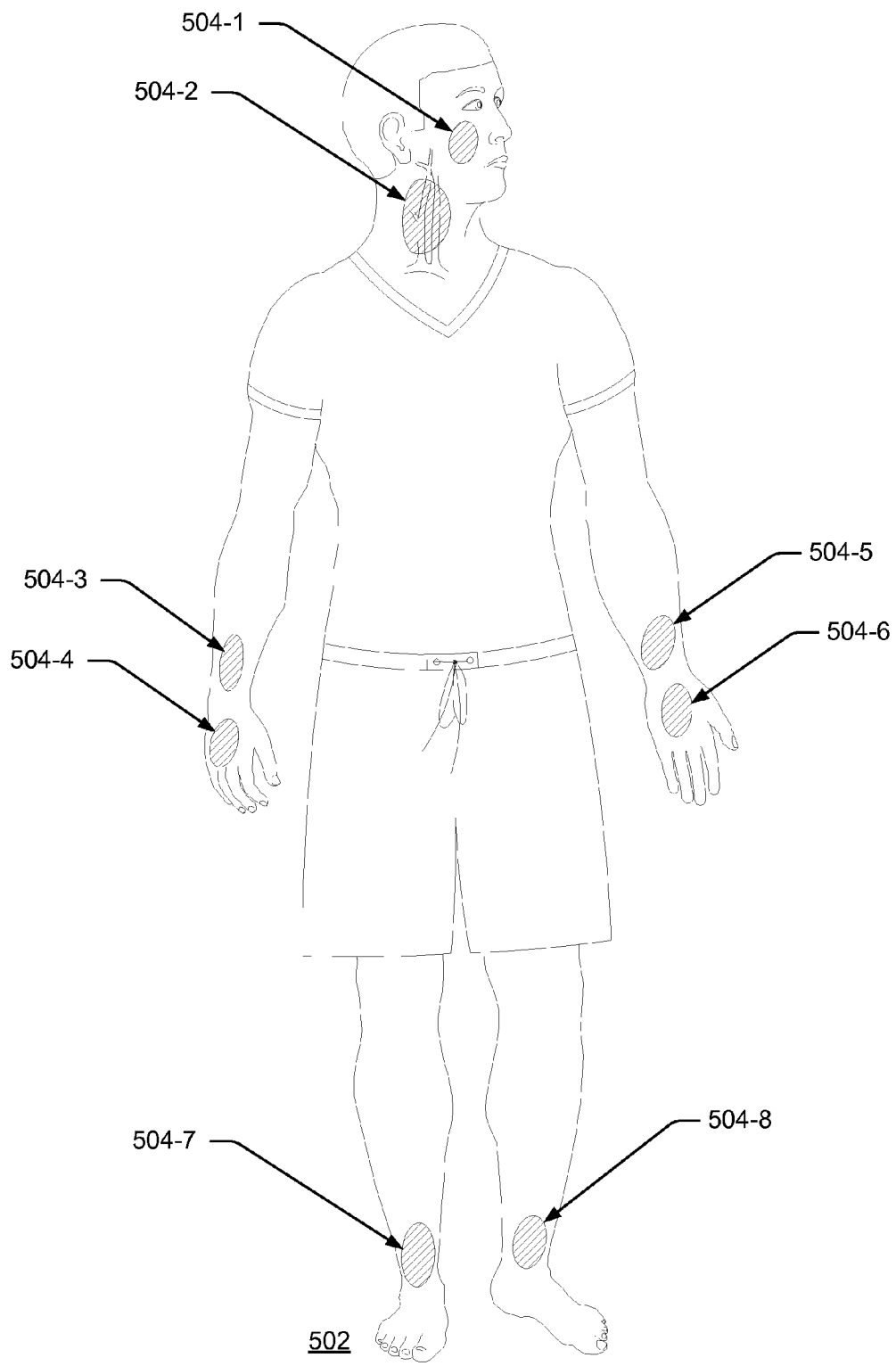
FIG. 5 illustrates a male patient having various regions of which images are captured by optical sensors.

By way of illustration, consider FIG. 5, which shows a male patient 502 having various regions 504 of which images are captured. These regions 504 include, by way example, a cheek region 504-1, a neck region 504-2, an outer wrist region 504-3, an outer hand region 504-4, an inner wrist region 504-5, a palm region 504-6, a front ankle region 504-7, and an inner ankle region 504-8, to name but a few. By way of an ongoing example, assume that one optical sensor captures a color change or displacement of skin at neck region 504-2 and another color change or displacement of skin at inner wrist region 504-5.

At 404, a circulatory distance is determined between the regions of the patient at which the colors or displacements are captured. This circulatory distance can be an approximation based on a linear distance between the regions, such as a linear distance based on an axial distance oriented relative to an axis of the patient's spine, or simply a vertical distance with the patient standing. In some cases, however, the techniques determine or approximate a circulatory distance based on an arterial-path distance. This arterial-path distance can be determined or approximated using an arterial structure of the patient or determined based on a skeletal structure of the patient, including automatically by optical visualization of the patient.

Figure 6:
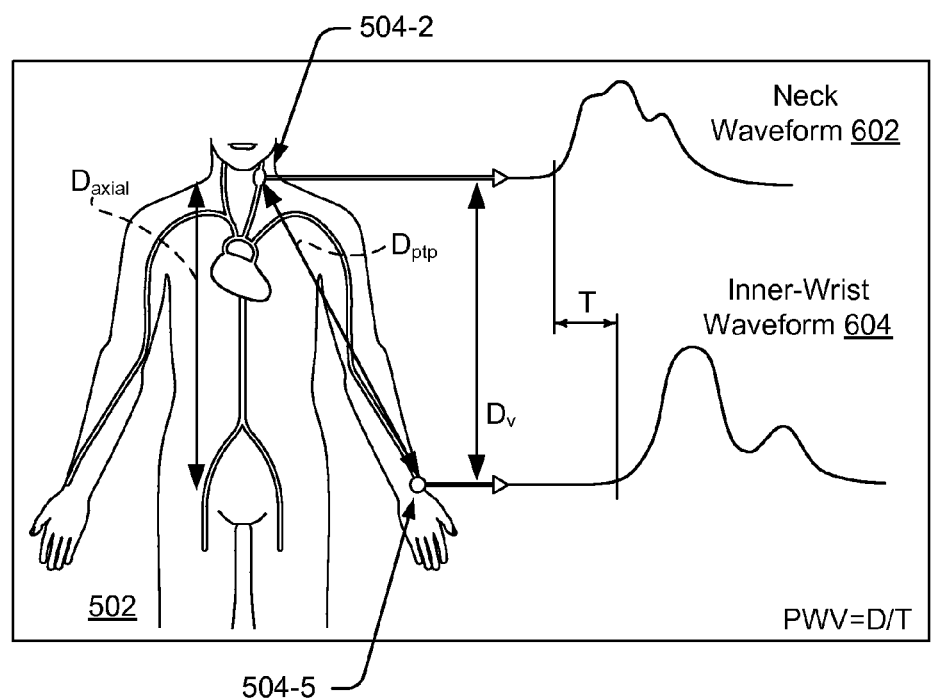
FIG. 6 illustrates various circulatory distances that can be used, along with time correlations, to determine a pulse-wave velocity.
Figure 6:
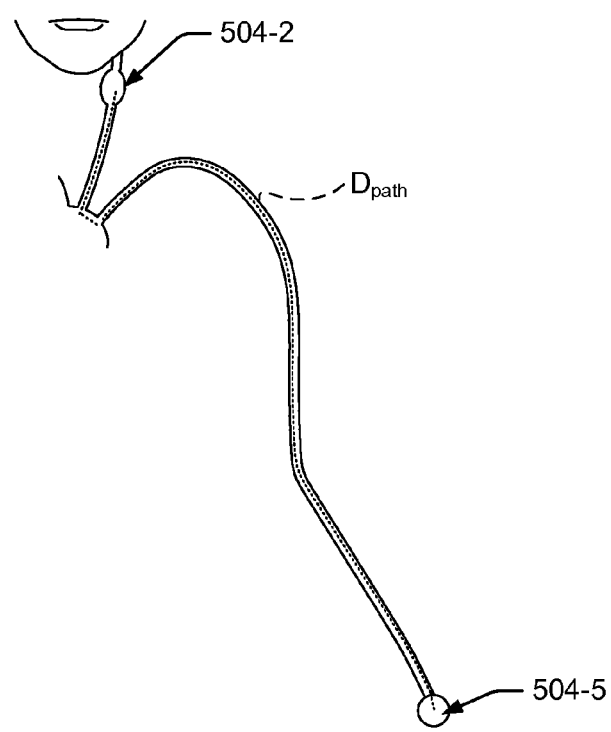

By way of illustration of the various circulatory distances that can be used, consider FIG. 6. Here assume that multiple images are captured of patient 502's neck region 504-2 (also shown in FIG. 5) sufficient to determine a neck waveform 602. Multiple images are also captured of inner wrist region 504-5 sufficient to determine an inner-wrist waveform 604. At operation 404, cardiovascular-function module 210 determines the circulatory distance from neck region 504-2 and inner wrist region 504-5 in one of the following four manners. In the first, a vertical distance $D_v$ is calculated with the patient standing. In the second, an axial distance $D_{axial}$ is calculated based on the distance relative to an axis of the patient's spine—here it is similar to the vertical distance, $D_v$, but if the person is oriented at an angle, the distances are different. In the third, cardiovascular-function module 210 calculates the distance as a point-to-point between the regions, here shown as $D_{ptp}$. In the fourth, cardiovascular-function module 210 calculates or approximates the distance that blood travels through patient 502's arteries, $D_{path}$. This arterial-path distance can be determined based on the arteries themselves or an approximation based on a skeletal structure or an overall body shape of the person. Data for skeletal structure and overall body shape can be determined using images captured for the regions and structures in between the regions, optically or otherwise. In some cases radar can be used that penetrates clothing to track bony surfaces, thereby providing a skeletal structure from which arterial distance can be approximated.

While not required, operation 404 may be performed, in whole or in part, using method 700 illustrated in FIG. 7, which is described following method 400 below. By way of overview, in this example method, the techniques determine one or more of the distances illustrated in FIG. 6.

The more-accurate distance calculations provide a better pulse-wave velocity, and thus indicate a current cardiovascular function. While potentially valuable, more-accurate distances are not necessarily required to show trends in cardiovascular function. Trends are provided by consistently calculated distances more than accurate distances, and for a specific individual, should not change significantly over time for same measurement points. If the measurement points vary due to visibility issues (such as clothing), then distance measurement estimates increase in importance for accurate trending.

At 406, a time correlation between capture of the colors and displacements is determined. This time correlation is between the instant of capture at the regions, as this time correlation is later used. Cardiovascular-function module 210 may determine the time correlation based on a time at which a maximum or minimum blood volume is determined for each of the regions, or some other consistent and comparable point in a waveform, such as a beginning of a pressure increase in the waveform (show in FIG. 6). In more detail, this time correlation can be considered a temporal distance between multiple images capturing some measure of cardiac operation, such as blood volume at each of the regions. Thus, by comparing various images for a region cardiovascular-function module 210 can determine a maximum, minimum, or median color at the region as well as at another region, and by comparing these and times at which each were taken, can determine the time correlation for a same heartbeat.

Note that waveforms 602 and 604 can be determined through color, or in some locations of the body, related waveforms can be determined through displacement. Cardiovascular-function module 210 can determine, based on a change in color to regions over time, a waveform. These color changes indicate a peak or crest of a wave based on blood content at the organ and thus can be used to determine a shape of the wave. While a shape of a wave can differ at different regions, they can still be compared to find a time correlation. In the case of lower-than-desired optical frame rates due to sensitivity or processing limitations, interpolation or curve fitting can be used to improve the estimate of the waveform for improved time correlation. Repeated measurements, which are time shifted relative to the pressure wave either naturally by the optical sampling frequency or intentionally by adjusting the sampling frequency, can build up a super-sampled estimate of the waveform. The higher timing-resolution waveform can be used for more-accurate timing measurements. Additionally, displacements, either through direct distance measurements or tangential shading, can show signals related to the pressure waveforms as the arteries and veins expand and contract. These waveforms can further reveal cardiac activity, such as valve timing, valve leakage (regurgitation), fibrillation, stroke volume, and the like.

At 408, a pulse-wave velocity for blood circulation through the patient is determined based on the circulatory distance and the time correlation, as well as the skin colors or displacements. As shown in FIG. 6, the time correlation is based on similar points in a waveform and the circulatory distance is some calculation or approximation of the distance blood travels from regions at which images are captured. In more detail, a pulse-wave velocity is the circulatory distance divided by the time correlation.

Pulse-wave velocity is a good measure of cardiac function. It can indicate, for example, an arterial stiffness of a patient (the faster the pulse-wave velocity, the higher the arterial stiffness), a blood pressure, and a mean arterial pressure for the patient. In more detail, the techniques can determine blood pressure based on the pulse-wave velocity using the Bramwell-Hill equation, which links pulse-wave velocity to compliance, blood mass density, and diastolic volume. Each of these are measures of cardiac function that can indicate a patient's cardiac health. As noted above, the techniques can provide these cardiac functions to a patient, thereby encouraging the patient to make changes or, in some cases, seek immediate medical care.

Note that, in some cases, three or more different regions are measured at operation 402. In these cases, cardiovascular-function module 210 may determine which of the regions are superior to others, such as due to data captured for those regions being noisy or incomplete or otherwise of inferior quality. Those that are superior can be used and the others discarded, or cardiovascular-function module 210 may weigh the determined pulse wave velocity between different regions based on the quality of the data used to determine those pulse wave velocities. This can be performed prior to or after recording those pulse wave velocities as described below.

Following determination of the pulse-wave velocity at operation 408, the techniques may proceed to record the pulse-wave velocity at operation 410 and the repeat operations 402-410 sufficient to determine a trend at operation 412. In some cases, however, the determined pulse-wave velocity is provided, at operation 414, to the patient or medical professional. Optionally, calibration data from an external sensor can be used to improve performance. For example, an external blood pressure monitor could be used to train the system to correlate PWV with blood pressure. The device could be captured through an electronic network (Bluetooth™ or the like) or the optical system could scan the user interface and perform OCR to read the results. Machine learning could be applied to create a patient specific model for estimating blood pressure from PWV.

At 412, a cardiovascular trend for the patient is determined based on multiple pulse-wave velocity measurements, such as comparing prior and later-time determined pulse-wave velocities. This can simply show a trend of pulse-wave velocities rising or falling, such as with velocity rising due to increased arterial stiffness. Multiple locations across the body can be measured to map changes over time. Cardiovascular-function module 210 may also determine other measures of cardiac function, such as changes in flow asymmetries or pulse pressure waveforms over time.

At 414, as noted, this trend determined at operation 412, or a pulse-wave velocity determined at operation 408, is provided to the patient or a medical professionals, e.g., patient 102 or 600 and medical professional 104, of FIG. 1 or 6.

In some cases skin color, skin displacement, or both are used by the techniques in method 400. Thus, color changes can indicate blood flow over time, as can displacement changes. Furthermore, use of color and displacement both can indicate an amount of blood in capillaries in the skin while displacement can indicate a change to a volume of the skin or an organ under the skin, such as vein or artery, and thus an amount of blood in the skin or near it can be determined.

Note also that the techniques may repeat operations of method 400 for various other regions. Doing so may aid in altering the pulse-wave velocity to improve its accuracy or robustness by determining another pulse-wave velocity between two other regions or between another region and one of the regions for which images are captured. Thus, the techniques may determine a pulse-wave velocity for the patient based on two pulse-wave velocities between regions, such as regions 504-3 and 504-1, 504-7 and 504-1, and/or 504-8 and 504-2.

Figure 7:
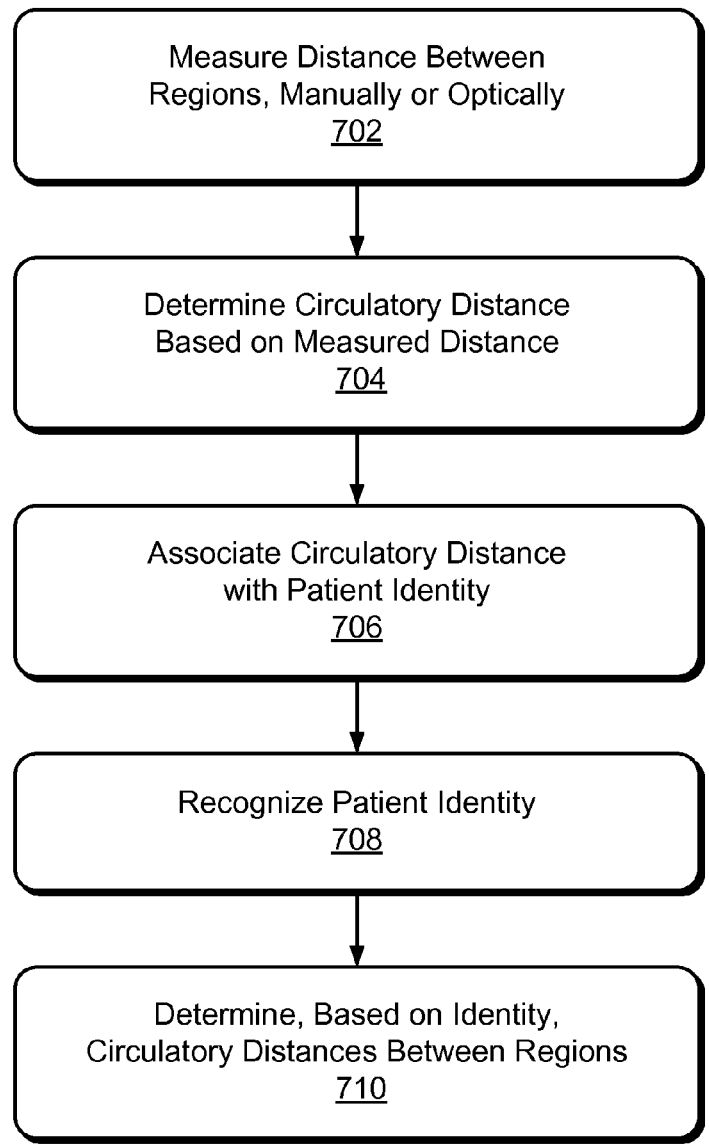
FIG. 7 illustrates a method for determining circulatory distances, such as those described in FIG. 6.

As noted above, method 400 can be supplemented, and operation 404 may be performed, in whole or in part, using method 700 illustrated in FIG. 7. In this example method, the techniques determine one or more of the distances illustrated in FIG. 6. For operations 702-706, a patient's circulatory distances between regions are establish for later use as a manner in which to calibrate the patient's distances. While calibration for a single sensing milieu to determined trends may not be required, use of different sensing milieus or to determine a cardiovascular function with quantitative precision both aid from use of calibration. Operation 708 and 710 can be used as one way in which the techniques may perform operation 404 of method 400.

At 702, a distance between various regions is measured, optically, manually, or in other manners. Consider, for example, capturing an image of patient 502 of FIG. 5. Assume that some physical data is available, such as a distance between the optical sensor capturing the image and patient 502, or a height of patient 502, and so forth. With this physical data, the distance can be determined from the image. Generally, this distance is from point-to-point, and is later analyzed for circulatory distance. Other manners can also or instead be used, such as a nurse measuring patient 502, either from point-to-point or along structures, such as from a wrist to an elbow, elbow to shoulder, and from shoulder to heart. A patient may also interact with optical sensor 106 and cardiovascular-function module 210 to calibrate distances between regions, such as standing at a particular location relative to optical sensor 106 and so forth. Various other technologies can be used as well, such as structured light optical sensors, radar, LIDAR, and SODAR (measuring distance through use of sound through air).

At 704, a circulatory distance is determined using the measured distance. In some cases the measured distance is simply used as the circulatory distance, such as measuring $D_{ptp}$ and then using $D_{ptp}$ (of FIG. 6) as the circulatory distance. As noted in part herein, however, other circulatory distances may be determined, such as measuring a point-to-point where patient 502's arm is bent, and thus calculating a fully extended point-to-point to maintain consistency of circulatory distance. Other examples include measuring $D_v$ and then, based on data about patient 502, determining an arterial-path distance ($D_{path}$).

At 706, these various determined circulatory distances are associated with the patient's identity. The identity of the patient can be entered, queried from the patient, or simply associated with some repeatable measure of identity, even if the person's name is not known. Examples include determining identity using fingerprints or facial recognition, and then associating distances with that fingerprint or facial structure.

At 708, the patient's identity is determined. This can be performed as part of operation 404. With this identity, at 710 circulatory distances between regions are determined. For example, cardiovascular-function module 210 may use facial recognition to identify patient 502 and, after determining patient 502's identity, find previously determined cardiovascular distances between each of regions 504 by simply mapping the relevant regions to previously stored distances. When cardiovascular time correlations are determined at operation 406, a pulse wave velocity can be determined using the mapped-to cardiovascular distance for the regions measured.

FIG. 8 depicts a method for assessing cardiovascular function using an optical sensor based on size, volume, or location of an organ or structure of a patient. In method 800, images are captured over 2 to 10 millisecond-range or faster timeframes, thereby providing multiple images relating to an organ or structure of the patient. Note that sub-millisecond timeframes can also be useful for measure acoustic vibrations and are optional. Method 800 may operate, in whole or in part, in conjunction with method 400, though this is not required.

At 802, structured light is projected onto an organ or structure of a patient. Note that this is optional, though in some cases use of structured light aids in accurate measurement of movement and displacement of a region of the patient. Alternatively, tangential light may be used to generate shadowing to detect skin displacement, or a coded light source could be used to reject external interference. For example, an alternating on and off light source at the frame rate would allow sampling and canceling of the background illumination. Further, light reflected from background objects or patient clothing can be used to track changes in lighting over time or in different conditions, e.g., daylight vs night, light bulb luminosity degradation over time, and so forth. With this data, ambient light and its effect on images captured can be calibrated and for which cardiovascular-function module 210 can adjust for the various methods described herein.

At 804, multiple images are received that capture an organ or structure of a patient. As noted, the images captured may include capture of structured light to aid in determining displacement using surface information captured. This surface information can be from one or multiple devices. These multiple images can be received from one or multiple optical sensors and over various timeframes, such as those captured at millisecond-range or faster timeframes.

At 806, changes in the size, volume, or location of the organ or structure of the patient are determined. These changes are determined by comparing sizes, volumes, or locations of the organ or structure of the patient recorded by the various multiple images captured over time. Note that these changes can be used in coordination with, or to compensate for, data from methods 400, and vice-versa. Thus, data from one portion of the body captured in any of the various manners described herein, can be used to compensate for other data, such as using a color or waveform determined at method 400 to compensate for motion artifacts in the data of method 800.

At 808, a cardiac function of the patient is determined based on the changes. This cardiac function can be one of the many described above, including heart rate, blood pressure, pulse-wave velocity, pressure volume loops, blood-volume and other asymmetries, and so forth, as well as respiration rate.

By way of a first example, consider a case where an asymmetry is determined between to different regions of the patient. In some cases this asymmetry is determined by blood-volume differences, which can be indicated by size or color. To determine an asymmetry, cardiovascular-function module 210 may compare the different cardiovascular pulse times of the regions, where one of the pulse times for a same heart beat is different, as it is further from the patient's heart.

Alternatively, the waveform's peak, median, or trough of blood volume can be accurately compared. Thus, assume that a right wrist and a left wrist of a patient have different blood volumes at each of their peaks, with one being a lower peak blood volume that the other, thereby indicating some difference in vascular function.

Cardiac function trends, as noted in part above, can greatly aid in helping patients maintain or change their habits to improve their cardiac health. Consider, for example, a trend showing a change to a cardiovascular function over weeks, months, or years using the techniques. This trend can show cardiac function in many ways superior to the best invasive cardiac testing because a trend need not require perfect accuracy—instead consistency is used. Furthermore, this can be performed by the techniques without interrupting the patient's day, making the patient perform a test, or requiring the patient to go see a medical professional. By so doing, many lives can be saved.

In more detail, consider the techniques in the context of FIGS. 1-3. Here various kinds of optical sensors 106 sense regions (e.g., regions 504 of FIG. 5) of a patient (e.g., patient 102 of FIG. 1 or patient 502 of FIGS. 5 and 6) through image capture elements 306. This sensor data (e.g., images) are then processed and/or stored by optics manager 310 (e.g., to mark the images with times), after which they are passed, through wired/wireless transceiver 308 as sensor data 112 to cardiovascular-function module 210 operating on computing device 108 of FIG. 2. Also passed are indications of the region and the times 212 at which the sensor data 112 was captured.

Cardiovascular-function module 210 then performs operations of method 400 and/or method 800 to determine cardiac function, as noted above. Consider, for example, a case where cardiovascular-function module 210 determines that a cardiac function meets or exceeds a safety threshold. Example safety thresholds include a blood pressure being too high, a heart rate being too rapid or irregular, or a low blood-oxygen level. This safety threshold can also be complicated or more difficult to determine, such as a patient's heart showing an end-diastolic volume ejected out of a ventricle during a contraction being less than 0.55 (this is a measure of ejection fraction (EF) and low fractions can indicate a heart attack is imminent). These are but a few of the many safety thresholds for cardiac function enabled by the techniques. If a safety threshold is exceeded, medical professional 104 (or family/caretaker) and patient 102 can be informed, such by operation 810 of method 800.

The preceding discussion describes methods relating to assessing cardiovascular function using an optical sensor for a human cardiovascular system. Aspects of these methods may be implemented in hardware (e.g., fixed logic circuitry), firmware, software, manual processing, or any combination thereof. These techniques may be embodied on one or more of the entities shown in FIGS. 1-3 and 9 (computing system 900 is described in FIG. 9 below), which may be further divided, combined, and so on. Thus, these figures illustrate some of the many possible systems or apparatuses capable of employing the described techniques. The entities of these figures generally represent software, firmware, hardware, whole devices or networks, or a combination thereof.

Example Computing System

Figure 9:
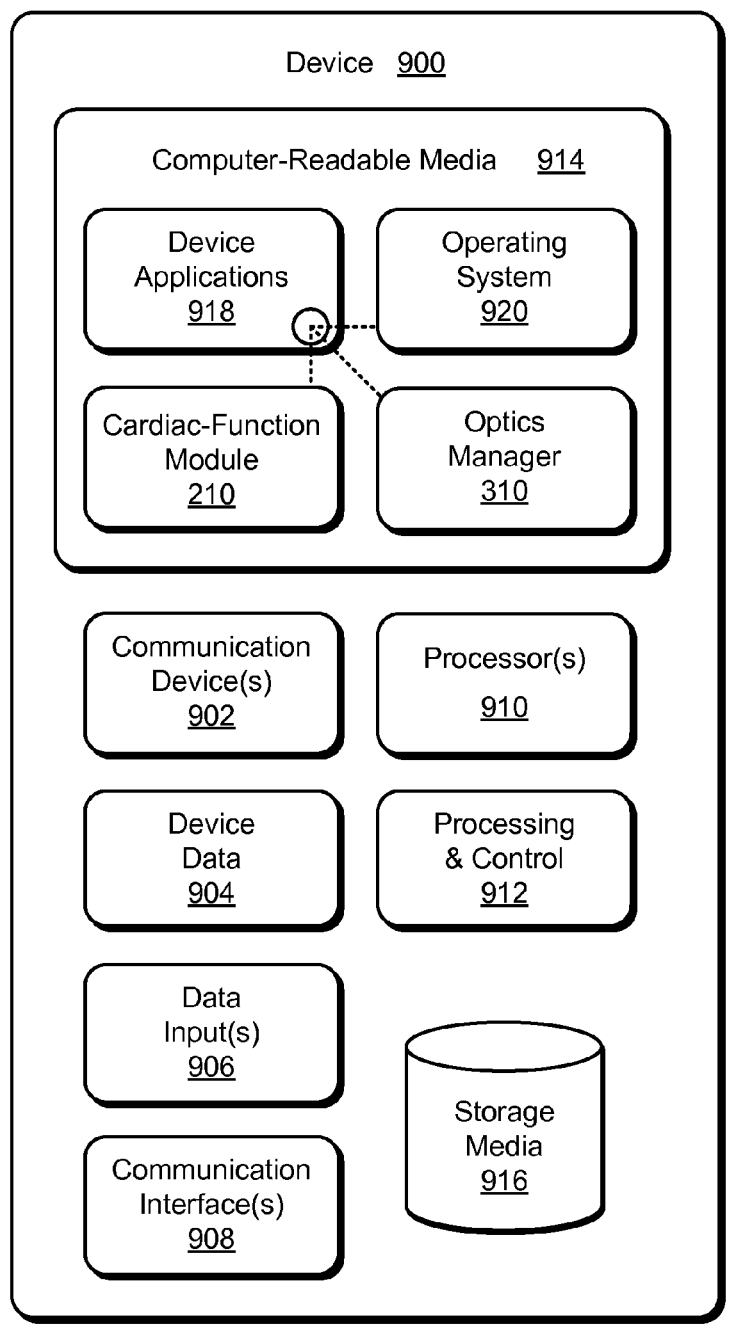
FIG. 9 illustrates an example device embodying, or in which techniques may be implemented that assess cardiovascular function using an optical sensor.

FIG. 9 illustrates various components of example computing system 900 that can be implemented as any type of client, server, and/or computing device as described with reference to the previous FIGS. 1-8 to implement techniques for assessing cardiovascular function using an optical sensor. In embodiments, computing system 900 can be implemented as one or a combination of a wired and/or wireless wearable device, System-on-Chip (SoC), and/or as another type of device or portion thereof. Computing system 900 may also be associated with a user (e.g., a patient) and/or an entity that operates the device such that a device describes logical devices that include users, software, firmware, and/or a combination of devices.

Computing system 900 includes communication devices 902 that enable wired and/or wireless communication of device data 904 (e.g., received data, data that is being received, data scheduled for broadcast, data packets of the data, etc.). Device data 904 or other device content can include configuration settings of the device, media content stored on the device, and/or information associated with a user of the device. Media content stored on computing system 900 can include any type of audio, video, and/or image data, including complex or detailed results of cardiac function determination. Computing system 900 includes one or more data inputs 906 via which any type of data, media content, and/or inputs can be received, such as human utterances, user-selectable inputs (explicit or implicit), messages, music, television media content, recorded video content, and any other type of audio, video, and/or image data received from any content and/or data source.

Computing system 900 also includes communication interfaces 908, which can be implemented as any one or more of a serial and/or parallel interface, a wireless interface, any type of network interface, a modem, and as any other type of communication interface. Communication interfaces 908 provide a connection and/or communication links between computing system 900 and a communication network by which other electronic, computing, and communication devices communicate data with computing system 900.

Computing system 900 includes one or more processors 910 (e.g., any of microprocessors, controllers, and the like), which process various computer-executable instructions to control the operation of computing system 900 and to enable techniques for, or in which can be embodied, assessing cardiovascular function using an optical sensor. Alternatively or in addition, computing system 900 can be implemented with any one or combination of hardware, firmware, or fixed logic circuitry that is implemented in connection with processing and control circuits which are generally identified at 912. Although not shown, computing system 900 can include a system bus or data transfer system that couples the various components within the device. A system bus can include any one or combination of different bus structures, such as a memory bus or memory controller, a peripheral bus, a universal serial bus, and/or a processor or local bus that utilizes any of a variety of bus architectures.

Computing system 900 also includes computer-readable media 914, such as one or more memory devices that enable persistent and/or non-transitory data storage (i.e., in contrast to mere signal transmission), examples of which include random access memory (RAM), non-volatile memory (e.g., any one or more of a read-only memory (ROM), flash memory, EPROM, EEPROM, etc.), and a disk storage device. A disk storage device may be implemented as any type of magnetic or optical storage device, such as a hard disk drive, a recordable and/or rewriteable compact disc (CD), any type of a digital versatile disc (DVD), and the like. Computing system 900 can also include a mass storage media device 916.

Computer-readable media 914 provides data storage mechanisms to store device data 904, as well as various device applications 918 and any other types of information and/or data related to operational aspects of computing system 900. For example, an operating system 920 can be maintained as a computer application with computer-readable media 914 and executed on processors 910. Device applications 918 may include a device manager, such as any form of a control application, software application, signal-processing and control module, code that is native to a particular device, a hardware abstraction layer for a particular device, and so on.

Device applications 918 also include any system components, modules, or managers to implement the techniques. In this example, device applications 918 include cardiovascular-function module 210 or optics manager 310.

CONCLUSION

Although embodiments of techniques for, and apparatuses enabling, assessing cardiovascular function using an optical sensor have been described in language specific to features and/or methods, it is to be understood that the subject of the appended claims is not necessarily limited to the specific features or methods described. Rather, the specific features and methods are disclosed as example implementations of these techniques.

What is claimed is:

1. A method comprising:
receiving, by a computing device and from one or more optical sensors operatively coupled to the computing device, multiple images captured external to a patient by the one or more optical sensors over millisecond-range or faster timeframes, the multiple images recording a color or displacement corresponding to an organ or structure of the patient;
calculating at least one of a change in size, a change in volume, or a change in location of the organ or structure of the patient by:
analyzing the multiple images to determine the color or displacement corresponding to the organ or structure in different said images;
correlating the determined color or displacement with associated times of the different said images; and
comparing the determined color or displacement associated with different said times to determine at least one of a maximum, minimum, or median of the determined color or displacement across the multiple images;
determining, based on the calculated at least one change in size, volume, or location, at least one measurement indicative of cardiac function of the patient; and
displaying a user interface to present the at least one measurement.

2. The method of claim 1, wherein the one or more optical sensors are hyperspectral cameras recording images in an ultraviolet, visible, or infrared optical wavelength and calculating the at least one change in size, volume, or location is based on the images recorded in the ultraviolet, visible, or infrared optical wavelength.

3. The method of claim 1, wherein the calculated at least one change in size, volume, or location indicates a blood force or mechanical vibration enabling a ballistocardiogram to be determined, and the method further comprises determining and providing the ballistocardiogram for the patient.

4. The method of claim 1, further comprising projecting structured light on regions of the patient corresponding to the organ or structure effective to enable capture of images having surface information enabling depth and surface changes for the organ or structure of the patient to be calculated.

5. The method of claim 4, wherein the images having the surface information are the multiple images and calculating the at least one change in size, volume, or location is based on the surface information.

6. The method of claim 4, wherein the images having the surface information are not the multiple images, and the method further comprises calculating the at least one change in size, volume, or location using both the multiple images and the images having the surface information.

7. The method of claim 1, further comprising:
determining the at least one measurement indicative of the cardiac function of the patient at a plurality of different times; and
determining a trend in cardiovascular health of the patient based on the determined measurements at the plurality of different times.

8. A system comprising:
a processor; and
a memory having stored thereon computer-readable instructions that are executable by the processor to perform operations comprising:
receiving, from one or more optical sensors external to a patient, multiple images captured over millisecond-range or faster timeframes by the one or more optical sensors, the multiple images recording a color or displacement corresponding to an organ or structure of the patient;
calculating at least one of a change in size, a change in volume, or a change in location of the organ or structure of the patient by:
analyzing the multiple images to determine the color or displacement corresponding to the organ or structure in different said images;
correlating the determined color or displacement with associated times of the different images;
comparing the determined color or displacement associated with different said times; and
determining at least one of a maximum, minimum, or median of the determined color or displacement across the multiple images based on the comparing;
determining, based on the calculated at least one change in size volume, or location, at least one measurement indicative of cardiac function of the patient; and
generating a user interface for display that is configured to present the at least one measurement.

9. The system of claim 8, wherein the operations further comprise displaying the generated user interface to present the at least one measurement.

10. The system of claim 8, wherein the one or more optical sensors are hyperspectral cameras recording images in an ultraviolet, visible, or infrared optical wavelength and calculating the at least one change in size, volume, or location is based on the images recorded in the ultraviolet, visible, or infrared optical wavelength.

11. The system of claim 8, wherein the calculated at least one change in size, volume, or location indicates a blood force or mechanical vibration enabling a ballistocardiogram to be determined, and the operations further comprise determining and providing the ballistocardiogram for the patient.

12. The system of claim 8, wherein the operations further comprise projecting structured light on regions of the patient corresponding to the organ or structure effective to enable capture of images having surface information enabling depth and surface changes for the organ or structure of the patient to be calculated.

13. The system of claim 12, wherein the images having the surface information are the multiple images and calculating the at least one change in size, volume, or location is based on the surface information.

14. The system of claim 12, wherein the images having the surface information are not the multiple images, and the operations further comprise calculating the at least one change in size, volume, or location using both the multiple images and the images having the surface information.

15. The system of claim 8, wherein the operations further comprise:
   determining the at least one measurement indicative of the cardiac function of the patient at a plurality of different times; and
   determining a trend in cardiovascular health of the patient based on the determined measurements at the plurality of different times.

16. A method implemented by a computing device, the method comprising:
   capturing multiple images external to a patient with one or more optical sensors operatively coupled to the computing device, the multiple images recording a color or displacement of at least one region of the patient that corresponds to an organ or structure of the patient;
   receiving, by the computing device and from one or more optical sensors, the multiple images;
   determining the color or displacement of the at least one region that corresponds to the organ or structure in different said images;
   correlating the determined color or displacement to associated times of the different said images;
   calculating at least one of a change in size, a change in volume, or a change in location of the organ or structure of the patient by comparing the determined color or displacement of the at least one region over the correlated times to determine at least one of a maximum, minimum, or median of the determined color or displacement of the at least one region across the multiple images;
   determining at least one measurement indicative of cardiac function of the patient based on the calculated at least one change in size, volume, or location; and
   displaying a user interface to present the at least one measurement.

17. The method of claim 16, wherein the one or more optical sensors are hyperspectral cameras recording images in an ultraviolet, visible, or infrared optical wavelength and calculating the at least one change in size, volume, or location is based on the images recorded in the ultraviolet, visible, or infrared optical wavelength.

18. The method of claim 16, wherein the calculated at least one change in size, volume, or location indicates a blood force or mechanical vibration enabling a ballistocardiogram to be determined, and the method further comprises determining and providing the ballistocardiogram for the patient.

19. The method of claim 16, further comprising projecting structured light on regions of the patient corresponding to the organ or structure effective to enable capture of images having surface information enabling depth and surface changes for the organ or structure of the patient to be calculated.

20. The method of claim 16, further comprising:
   determining the at least one measurement indicative of the cardiac function of the patient at a plurality of different times; and
   determining a trend in cardiovascular health of the patient based on the determined measurements at the plurality of different times.

* * * * *